United States Patent [19]
Friedman et al.

[11] Patent Number: 5,750,142
[45] Date of Patent: May 12, 1998

[54] DRY COMPOSITIONS FOR PREPARING SUBMICRON EMULSIONS

[75] Inventors: Doron Friedman, Karmei-Yosef; Yanir Aldouby, Modiin, both of Israel

[73] Assignee: Pharmos Corporation, New York, N.Y.

[21] Appl. No.: 840,177

[22] Filed: Apr. 11, 1997

Related U.S. Application Data

[60] Continuation of Ser. No. 486,791, Jun. 7, 1995, abandoned, which is a division of Ser. No. 16,913, Feb. 12, 1993, Pat. No. 5,472,706.

[30] Foreign Application Priority Data

Feb. 18, 1992 [IL] Israel ......................... 101007

[51] Int. Cl.$^6$ ......................... A61K 9/127
[52] U.S. Cl. .................. 420/450; 514/937; 514/938; 514/939; 514/943; 264/4.1; 264/4.3
[58] Field of Search ................ 424/450; 514/937, 514/938, 939, 943; 264/4.1, 4.3

[56] References Cited

U.S. PATENT DOCUMENTS

| | | | |
|---|---|---|---|
| 4,178,695 | 12/1979 | Erbeia | 34/5 |
| 4,616,047 | 10/1986 | Lafon | 523/105 |
| 4,647,586 | 3/1987 | Mizushima et al. | 514/532 |
| 5,004,756 | 4/1991 | Ogawa et al. | 514/655 |

FOREIGN PATENT DOCUMENTS

| | | |
|---|---|---|
| A 0 211 257 | 2/1987 | European Pat. Off. |
| A 0 211 258 | 2/1987 | European Pat. Off. |
| 1227744 | 4/1971 | United Kingdom. |
| 1310824 | 3/1973 | United Kingdom. |
| 1382641 | 8/1973 | United Kingdom. |

*Primary Examiner*—Gollamudi S. Kishore
*Attorney, Agent, or Firm*—Pennie & Edmonds

[57] ABSTRACT

The present invention relates to dry, stable compositions which can be reconstituted to form pharmaceutical or cosmetic emulsions, and to methods for making such compositions. An emulsion is formed from about 0.2 to 25 weight percent of a first component of an oil, about 0.1 to 5 weight percent of a second component of an emulsifier, about 0.25 to 25 weight percent of a cryoprotectant of an amino compound, such as one or more amino acids, peptides or protein hydrolysates, and an aqueous component, wherein the amino compound is present in an amount that is equal to or greater than that of the first component. Optionally, a co-emulsifier, a suspension agent, a preservative, an antioxidant and a drug can be added to these emulsions. Thereafter, the emulsion is lyophilized to form dry compositions that have from about 40 to about 90 weight percent of the amino compound; from about 0.1 to about 20 weight percent of the emulsifier; and from about 0.2 to about 40 weight percent of the oily component. By combining the dry composition with an appropriate quantity of an aqueous liquid, the composition is reformed as an oil-in-water emulsion.

39 Claims, No Drawings

DRY COMPOSITIONS FOR PREPARING SUBMICRON EMULSIONS

This is a continuation of application Ser. No. 08/486,791 filed Jun. 7, 1995, now abandoned, which is a division of application Ser. No. 08/016,913 filed Feb. 12, 1993, now U.S. Pat. No. 5,472,706.

FIELD OF THE INVENTION

The invention relates to dry compositions which are easily reconstituted with water to form submicron oil-in-water emulsions for use in the administration of pharmaceuticals and cosmetics, and to methods for making such dry compositions.

BACKGROUND OF THE INVENTION

Oil-in-water emulsions have particular utility for the administration of drugs, cosmetics or other active agents to subjects, but are disadvantageous in that such emulsions have certain drawbacks with regard to their manufacture, transportation and storage. These include the bulk and weight of the water which is used to keep the oil in suspension, limited long term storage stability of the emulsion, the limited range of concentrations in which such emulsions are available and the risk of microbial growth in the aqueous phase, which can be an especially fertile breeding ground for microorganisms when amino acids or carbohydrates are included.

Lyophilization is a well known technique for processing and storage of moisture sensitive compounds. This methodology is employed in various applications in the food and pharmaceutical industries. For example, U.S. Pat. No. 4,616,047 relates to oral emulsions that are prepared by a method which includes the steps of preparing a lipid phase by stirring at a temperature of 80° C. or less, preparing an aqueous phase by stirring an organic filler or thickening agent with water at a temperature of 80° C. or less, introducing the lipid phase into the aqueous phase to form a homogeneous emulsion, distributing the emulsion into alveolar packs, freezing the contents of the packs at a temperature of between −20° and −50° C., and lyophilizing the frozen contents at between 80 and 0.13 Pa with a heat supply that is always lower than the melting temperature of the components. A pharmaceutically active substance can be incorporated into the emulsion prior to distribution into the alveolar packs.

Prior attempts to lyophilize oil-in-water emulsions, however, failed to preserve the original mean droplet size after reconstitution. Furthermore, enhanced bioavailability of the drug is achieved when the mean droplet size is in the submicron range.

In addition, successful lyophilization usually requires the use of large amounts of carbohydrates which may cause hypertonic solutions and high susceptibility for microbial contamination. For example, European Patent 211,257 relates to emulsion compositions that comprise carbohydrates which in some instances may be dangerous for diabetic patients and on some occasions are hyperosmotic after reconstitution. These emulsions are thus intended only for parenteral use and contain hydrophobic drugs.

It is also difficult to stabilize oil-in-water emulsions for the commercially desired two-year shelf-life. While this goal can sometimes be achieved if the emulsions are stored refrigerated, the use of refrigeration causes limitations on the distribution of the product. Moreover, the addition of drugs to emulsions generally results in increased instability and precludes a reasonable commercial product.

Therefore, it would be advantageous, both practically and economically, if emulsions could be produced as a dry product which can be reconstituted prior to use in order to facilitate the transport, storage and stability of such emulsions. It would also be desirable to provide an oil-in-water emulsion composition which is storage-stable, which can be sterilized easily, which is easily prepared in any desired concentration and which eliminates the opportunity for microbial growth if it becomes contaminated.

SUMMARY OF THE INVENTION

The present invention relates to a lyophilized composition comprising from about 40 to about 90 weight percent of an amino compound; from about 0.1 to about 20 weight percent of a emulsifier; and from about 0.2 to about 40 weight percent of a oily component, the components being present in combination such that, when combined with an appropriate quantity of an aqueous liquid, the composition forms an oil-in-water emulsion. The amino compound may be a straight or branched amino acid or a nontoxic salt or ester thereof, a peptide or a compound which includes one or more amino groups. Preferred amino acids include glycine, leucine, isoleucine, lysine, methionine, phenylalanine, threonine, tryptophan, valine, alanine, arginine, histidine, proline, serine, tyrosine, taurine or carnitine, while preferred amino compounds include niacinamide or creatinine as well as peptides or protein hydrolysates. The use of such amino compounds provides superior performance with respect to the droplet size of the reconstituted product. This allows submicron emulsions having a mean droplet size of about 0.05 to 0.5 μm to be easily attained upon reconstitution.

These dry compositions are formed from oil-in-water emulsions comprising about 0.2 to 25 weight percent of a first component of an oil, about 0.1 to 5 weight percent of a second component of an emulsifier, about 0.25 to 25 weight percent of a cryoprotectant of an amino compound and an aqueous component, wherein the amino compound is present in an amount that is equal to or greater than that of the first component. If desired, a co-emulsifier, preferably of a non-ionic surfactant can be included in an amount of about 0.1 to 5%. A suspending agent, a preservative, an antioxidant and one or more drugs can also be included in these formulations.

The invention also relates to a method of making a lyophilized composition which comprises lyophilizing one of the emulsions described above, as well as to the dry lyophilized compositions which are made by such method.

Furthermore, the invention relates to the method of making an emulsion by adding a suitable aqueous liquid to one of these lyophilized compositions. The aqueous liquid for reconstituting these emulsions may be Water for Injection, U.S.P.; 0.9% Sodium Chloride Injection, U.S.P.; or 5% Dextrose Injection, U.S.P. Generally, less aqueous liquid is needed to make the emulsion than that which was removed when making the lyophilized composition, although the dry compositions can be dissolved to any desired concentration and osmolarity. Also, the aqueous liquid may be added to the lyophilized composition with mixing to form the emulsion.

DETAILED DESCRIPTION OF THE INVENTION

The invention relates to a dry, stable composition of matter having a long shelf-life which can be contacted with water or with an aqueous medium so as to result in an emulsion that comprises a preponderance of submicron size droplets. The emulsion is essentially an oil-in-water emulsion. The invention further relates to a process for the preparation of such stable dry compositions and oil-in-water emulsions. The compositions of this invention contain no carbohydrates and may incorporate all kinds of drugs, including those which are hydrophobic as well as amphiphilic, and mixtures thereof. These compositions have utility as parenteral, oral or topical emulsion vehicles for the administration of oil-soluble, water insoluble or amphiphilic pharmaceutical compounds.

An emulsion is a dispersion of oil in water ("o/w"), and can be defined as either a macroemulsion or a microemulsion. A macroemulsion is a cloudy turbid composition having an oil-droplet size of 0.5 to 100 µm and is generally thermodynamically unstable. In comparison, a microemulsion is a translucent to transparent composition having a droplet size of 0.005 to 0.5 µm, is thermodynamically stable and is generally self emulsifying. See, e.g., Friberg et al. (1987) Microemulsions Structure and Dynamics, CRC Press Inc., Boca Raton, Fla., pp. 154. Also, the proportion of surfactants to oil required to generate microemulsions is generally much higher than in macroemulsions.

The term "submicron" is used herein to mean a size of about 0.05 to 0.5 µm, and preferably about 0.1 to 0.3 µm. Thus, a submicron emulsion having droplets of these sizes would be smaller than those of a classical macroemulsion, which has droplet sizes of above 0.5 µm, but generally larger than those of a classical microemulsion, which, for practical purposes, has droplet sizes of less than 0.1 µm.

These submicron emulsion can easily be sterilized by filtration, for example, in 0.45 µm and/or 0.22 µm filters, are more stable in long-term storage and can better withstand sterilization in an autoclave.

The oil-in-water emulsions of the present invention are dispersions of droplets or colloidal particles in an aqueous medium, with the colloid particles having an oily core surrounded by an interfacial film of the emulsifiers and co-emulsifiers (i.e. surface acting agents or surfactants). For clarity in understanding the present invention, the following terms will be used:

"aqueous phase"—to denote the aqueous solution in which the droplets or colloid particles are dispersed;

"oily phase"—to denote the oily cores of the droplets or colloidal particles; and "amphiphilic phase"—to denote the interfacial films of emulsifier and surfactant surrounding the oily phase of the droplets or colloidal particles.

The essential components of the initial oil-in-water emulsion include an oil, an emulsifier and a cryoprotectant. Optionally, a co-emulsifier (or surfactant), a suspending agent, a preservative or an antioxidant can be included in these emulsions. As explained below, the drug can be added to the aqueous phase, the amphiphilic phase or the oil phase either before or after formation of the emulsion.

The cryoprotectant is preferably an amino compound. Suitable amino compounds include amino acids (primary, secondary, tertiary) or compounds having one or more amino groups, such as niacinamide or creatinine. The amino acids administered in the compositions of this invention can include, without limitation, leucine, isoleucine, lysine, methionine, phenylalanine, threonine, tryptophan, valine, alanine, arginine, histidine, proline, serine, tyrosine, glycine, taurine and carnitine, as the L-, D-, or racemic forms, as well as nontoxic salts and esters thereof. Most preferred are the L-acids, and their nontoxic salts and esters.

Although a single amino acid can be used to formulate the present compositions, it is possible and often preferred to use mixtures of two or more of these amino acids. In this regard, it is advantageous to use peptides or protein hydrolysates since they include multiple amino acids and/or peptides.

The amino acids added to the compositions of this invention also preferably comprise branched chain amino acids, which are reported to facilitate normalization of plasma amino acid levels, particularly in debilitated or liver-damaged patients.

The amino compound or compounds are generally present in the emulsion at a concentration of from about 0.25 to 25 weight percent, preferably about 0.5 to 12 weight percent, and more preferably about 1 to 10 weight percent. The amount of amino compound used should be less than that which would disrupt the emulsion while also being commensurate with the application intended. In addition, the amount used should be soluble. One skilled in the art can conduct routine tests to determine the optimum concentration.

The oil component may be a vegetable oil, a synthetic oil, a mineral oil or a medium chain triglyceride (MCT) oil, i.e. a triglyceride oil in which the carbohydrate chain has 8–12 carbons, or a combination of two or three of such oils. Although MCT oil can be considered as a component of vegetable oil, it is separately identified herein because of its particular utility as a preferred oil for use in the present emulsions. In addition, MCT oil is available commercially. Examples of such MCT oils include TCR (trade name of Societe Industrielle des Oleagineaux, France for a mixture of triglycerides wherein about 95% of the fatty acid chains have 8 or 10 carbons) and MIGLYOL 812 (trade name of Dynamit Nobel, Sweden for a mixed triester of glycerine and of caprylic and capric acids). Examples of vegetable oils include soybean oil, cotton seed oil, olive oil, sesame oil and castor oil. The mineral oils may be natural hydrocarbons or their synthetic analogs. Oily fatty acids, such as oleic acid and linoleic acid, fatty alcohols, such as oleyl alcohol, and fatty esters, such as sorbitan monooleate and sucrose mono- di- or tri-palmitate, can be used as the oil component, although these are not as preferred as the other oils mentioned above. Other lipids which can be used in the compositions of this invention include synthetic and semi-synthetic mono-, di- and/or triglycerides, triglycerides prepared by solvent or thermal fractionation of natural, synthetic or semisynthetic triglycerides, and triglycerides prepared by interesterification and/or directed or random rearrangement. The oil component is generally present at a concentration of from about 0.2 to 25 weight percent, preferably about 0.4 to 10 weight percent, and more preferably about 0.6 to 8 weight percent.

For optimum results, the amino compound and oil component are present at a weight ratio of about 0.3/1 to 20/1, respectively, and preferably about 0.4/1 to 15/1. The most preferred ratios are within the range of about 0.5/1 to 12.5/1. Generally, the use of mixtures of amino acids, peptides or protein hydrolysates require a lower weight ratio.

The amphiphilic phase includes the emulsifiers and, if used, the co-emulsifiers. Preferred emulsifiers include a phospholipid compound or a mixture of phospholipids. Suitable components include lecithin; EPICURON 120 (Lucas Meyer, Germany) which is a mixture of about 70% of phosphatidylcholine, 12% phosphatidylethanolamine and about 15% other phospholipids; OVOTHIN 160 (Lucas Meyer, Germany) which is a mixture comprising about 60% phosphatidylcholine, 18% phosphatidylethanolamine and 12% other phospholipids; a purified phospholipid mixture; LIPOID E-75 or LIPOID E-80 (Lipoid, Germany) which is a phospholipid mixture comprising about 80% phosphatidylcholine, 8% phosphatidylethanolamine, 3.6% non-polar lipids and about 2% sphingomyelin. Purified egg yolk phospholipids, soybean oil phospholipids or other purified phospholipid mixtures are useful as this component. This listing is representative and not limiting, as other phospholipid materials which are known to those skilled in the art can be used. The emulsifier is present in an amount of about 0.1 to 5 weight percent, preferably about 0.2 to 4 weight percent and more preferably about 0.25 to 2.5 weight percent.

The co-emulsifiers can be used to enhance the formation of the emulsion. This component may be a surface active agent or surfactant, preferably those which are non-ionic, and one skilled in the art can conduct routine tests to select specific compounds for any particular emulsion. Generally, the surfactant is a non-ionic alkylene oxide condensate of an organic compound which contains one or more hydroxyl groups. For example, ethoxylated and/or propoxylated alcohol or ester compounds or mixtures thereof are commonly available and are well known to those skilled in the art. Suitable surfactants include, but are not limited to, TYLOXAPOL; POLOXAMER 4070; POLOXAMER 188; POLYOXYL 40 Stearate; POLYSORBATE 80, and POLYSORBATE 20, as well as various compounds sold under the trade name TWEEN (ICI American Inc., Wilmington, Del., U.S.A.), PLURONIC F-68 (trade name of BASF, Ludwigshafen, Germany for a copolymer of polyoxyethylene and polyoxypropylene). Preferred surfactants also include polyoxyethylated oils or poloxamines. The TYLOXAPOL and TWEEN surfactants are most preferred because they are FDA approved for human use. The co-emulsifier is present in an amount of about 0.1 to 5 weight percent, preferably about 0.2 to 4 weight percent and more preferably about 0.25 to 2.5 weight percent.

A suspending agent may optionally be included to protect the emulsion during the drying stage, as well as to control the droplet size of the reconstituted emulsion so that it is retained in the submicron range. Suitable suspending agents include polyvinyl alcohol ("PVA"), polyvinyl pyrrolidone ("PVP"), gelatin, pectin, methyl cellulose, glycols such as polyethylene or polypropylene glycols or mixtures thereof. This component, when used, is generally in the range of about 0.1 to about 5 weight percent.

The aqueous component will be the continuous phase of the emulsion and may be water, saline or any other suitable aqueous solution which can yield an isotonic and pH controlled preparation.

A drug may also be included in the aqueous or oily phases of these emulsions. For example, the compositions of this invention can be formulated so that the discontinuous phase of the reconstituted emulsion contains one or more lipophilic pharmaceutically active agents ("lipophilic drugs"), either alone or dissolved in pharmaceutically acceptable lipids. By "lipophilic" herein is meant agents which are relatively insoluble in water but soluble in one or more of the fat solvents (benzene, chloroform, acetone, ether, hexane, etc.). In particular, the lipid-containing compositions can be used as vehicles for pharmaceutically active agents having lipid component:water partition coefficients of at least 2:1.

Compositions in which the discontinuous phase of the reconstituted emulsion consists essentially of a lipophilic drug or combination of lipophilic drugs avoid the use of a separate lipid vehicle for the drug, minimize the volume of a unit dose of the drug or drugs, and reduce the risk of toxic effects which might be associated with other vehicles which would otherwise be used.

Lipophilic drugs used in the compositions of this invention are preferably selected from the group consisting of general anesthetics, local anesthetics, hypnotics, sedatives and anxiolytics, antidepressants, anticonvulsants, narcotic analgesics and narcotic antagonists, nonsteroidal antiinflammatory drugs, anticholinesterases, sympathomimetics and parasympathomimetics, ganglionic stimulating and blocking agents, neuromuscular blocking agents, antimuscarinic agents, adrenergic blocking agents, autacoids and autacoid antagonists, digitalis and digitalis congeners, diuretics and saliuretics, antibiotics and antimicrobials, antineoplastics, immunosuppressants and immunomodulators, hemoglobin and hemoglobin derivatives and polymers, hormones and hormone antagonists, and fat-soluble vitamins, and combinations thereof. These terms are used in the sense commonly employed in standard reference test in the pharmaceutical arts, in particular, Gilman, Goodman and Gilman, *The Pharmacological Basis of Therapeutics*, 6th Ed. (MacMillan, New York, 1980), the disclosures of which are hereby incorporated herein by reference.

In particular, the general anesthetics can include, without limitation, diethyl ether, divinyl ether, fluroxene, methoxyflurane, halothane, etomidate, anesthetic steroids, enflurane, isoflurane, and combinations thereof.

Similarly, local anesthetics are preferably selected from cocaine, procaine, lidocaine, bupivacaine, chloroprocaine, dibucaine, etidocaine, mepivacaine, prilocaine, cyclomethycaine, hexylcaine and pramoxine, and combinations thereof.

The category of hypnotics, sedatives and anxiolytics includes the barbiturates, such as thiopental and phenobarbital; the benzodiazepines, such as diazepam and chlorazepate; the butyrophenones, such as droperidol and haloperidol; the phenothiazines, such as chlorpromazine and prochlorperazine; the thioxanthines, such as chlorprothixene; as well as the agents loxapine, molindone, chloral hydrate, chloral betaine, ethchlorvynol, ethinamate, glutethimide, meprobamate, methaqualone, methyprylon, paraldehyde, and triclofos; and combinations of any of the foregoing.

An antidepressant can be selected from imipramine, desipramine, amitriptyline, nortriptyline, doxepin, protriptyline, isocarboxazid, phenelzine and tranylcypromine, and combinations these agents.

Anticonvulsants include, without limitation, phenytoin, mephenytoin, ethotoin, primidone, carbamazepine, ethosuximide, methsuximide, phensuximide, valproic acid, valproates, trimethadione, paramethadione, and phenacemide, and combinations thereof.

Many nonsteroidal antiinflammatory drugs are preferentially soluble in lipids, including, without limitation, the salicylates, the vicinal and geminal organophosphonates, the gentisates, phenylbutazone, indomethacin, oxyphenbutazone, antipyrine, aminopyrine, apazoner acetaminophen, phenacetin, sulindac, flufenamates, mefenamates, tolmetin, ibuprofen, naproxen, fenoprofen, flurbiprofen, ketoprofen, colchicine and allopurinol, and combinations of these agents, although most are not commonly used in combination.

Compositions can also be formulated according to this invention wherein the discontinuous lipid phase contains a sympathonmimetic selected from the catecholamines, such as epinephrine and isoproterenol; amphetamines, including methamphetamine and hydroxyamphetamine; and the agents ephedrine, mephentermine, metaraminol, phenylephrine, methoxamine, methoxyphenaminer metaproterenol, and terbutaline; and combinations of any of the foregoing.

Adrenergic blocking agents useful in the practice of this invention include the alpha-adrenergic blockers, such as phenoxybenzamine; beta-adrenergic blockers, such as propranolol; adrenergic neuron blockers, such as guanethidine and bretylium; and combinations of these agents.

Autacoids as used herein refers to the natural and synthetic histamines, and 5-hydroxytryptamine, and combinations thereof. Similarly, autacoid antagonists are selected from histamine ($H_1$)-receptor blockers, histamine ($H_2$)-receptor blockers, and 5-hydroxytryptamine antagonists, such as alkaloids, lysergic acid derivatives, and cyproheptadine, as well as compatible combinations of these compounds.

A variety of diuretic or saluretic materials can be used in the practice of this invention, including those selected from the carbonic anhydrase inhibitors, such as acetazolamide; the benzothiadiazides, such as hydrochlorothiazide and methyclothiazide; and the agents ethacrynic acid, furosemide, bumetanide, muzolimine, spironolactone, triamterene, amiloride, ticrynafen and indacrynic acid, and combinations thereof.

Antimicrobial or antibiotic compounds useful in the practice of this invention include the penicillins, whether natural or synthetic; erythromycins, sulfonamides, cephalosporins, aminoglycosides, tetracyclines, chloramphenicol, isoniazid, rifamycins, pyrazinamide, cycloserine, viomycin, lincomycins, clindamycin, spectinomycin, polymyxins, vancomycin, nystatin, amphotericin B, flucytosine, griseofulvin, amantadine, methisazone, vidarabine, idoxuridine, acyclovir and interferon, and combinations thereof.

Antineoplastic agents include a variety of classes of compounds, such as ethyleneimine derivatives, alkyl sulfonates, nitrosoureas, triazones, folic acid analogs, pyrimidine analogs, purine analogs, vinca alkaloids, 1-asparaginase, dactinomycin, daunorubicin, doxorubicin, bieomycin, mithramycin, mitomycin, platinum coordination complexes, substituted ureas, procarbazine, mitotane and tamoxifen, and combinations thereof.

Cyclosporin is a principal example of the immunomodulators and immunosuppressants which can be used.

Hemoglobin and hemoglobin derivatives and polymers includes human, animal or synthetic hemoglobin per se as well as derivatives of human, animal or synthetic hemoglobin. Derivatives include hemoglobin oligomers and polymers, liposomal hemoglobin, and hemoglobin linked to other carrier or active compounds or polymers, such as hemoglobin linked to 2-nor-2-formylpyridoxal 5'-phosphate. These compositions can also be used as vaccines or blood substitutes.

Many hormones and synthetic derivatives are readily lipid soluble, particularly the synthetic steroid hormones. However, this class also includes growth hormone, prolactin, placental lactogen, luteinizing hormone, follicle stimulating hormone, thyrotropin, chorionic gonadotropin, chorionic thyrotropin, corticotropin, alpha- and beta-melanocyte stimulating hormones, beta- and gamma-lipotropins, endorphins, enkephalins, estrogens, progestins, androgens and anabolic steroids, glucocorticoids and glucocorticoid derivatives, mineralocorticoids and mineralocorticoid derivatives, insulin, glucagon, parathyroid hormone, thyroid hormone and calcitonin. Combinations of the foregoing hormone can also be used where appropriate.

The fat-soluble vitamins overlap some of the foregoing categories to a certain extent. As examples, Vitamin E is tocopherol antioxidant, and Vitamin D (calciferol) can properly be classified as a hormone. The fat soluble vitamins also encompass the carotenes, including Vitamin A and precursors; synthetic califerols and tocopherols, Vitamin K, including the menaquinones, phytonadione and menadione and combinations thereof.

Additional drugs which can be used include various anti-glaucoma drugs, such as beta-adrenergic blockers or other autonomic system drugs, anesthetics, steroids, non-steroidal anti-inflammatory drugs, antibiotic drugs, anti-fungal drugs, antiviral drugs or combinations thereof. If desired, the compositions of the present invention may also include additional drugs such as β-adrenergic blockers, cannabinoids, cholinesterase inhibitors, sympathomimetic agents or carbonic anhydrase inhibitors. Water soluble drugs such as timolol and pilocarpine (3-ethyldihydro-4-[(1-methyl-1H-imidazole-5-yl)methyl]-2(2H)-furanon) or water insoluble drugs, such as indomethacin, betaxolol and adaprolol are specific examples of drugs which can be used for ophthalmic formulations.

The term "effective amount" is used herein to denote an amount of a drug which is effective in exerting a pharmaceutical effect on the subject. The drug is typically present in an amount of about 0.01 to 2% by weight of the composition, preferably about 0.1 to 1%. Depending upon whether the drug is hydrophilic or hydrophobic, it will be physically present in the oil phase, the amphiphilic phase or the aqueous component.

"Pharmaceutically acceptable" is used herein to refer to those materials which are, within the scope of sound medical judgment, suitable for use in contact with the tissues of humans and lower animals without undue toxicity, irritation, allergic response, and the like, commensurate with a reasonable benefit/risk ratio, and effective for their intended use in the composition. It is preferred for each component to be pharmaceutically acceptable so that these compositions can be administered to humans.

Although they contain only conventional emulsifiers employed at their usual levels, the compositions of this invention are highly storage stable, since they can be kept for extended periods in dry form. Also, these dry products can be sterilized by gamma radiation without affecting the performance of the emulsion when used.

Also according to the desires of the formulator, the compositions of this invention can be formulated such that the aqueous continuous phase of the reconstituted emulsion comprises one or more solutes selected from electrolytes, water-soluble vitamins and water-soluble trace elements, and mixtures thereof. Electrolytes such as sodium, potassium, magnesium, calcium, lithium, ammonium, phosphorus, chloride, acetate, sulfate, carbonate, and phosphate, in pharmaceutically acceptable amounts are typical. In measuring or calculating the electrolyte content of the solutions, the electrolyte equivalents of the amino acids present in the formulation should be included.

The water-soluble vitamins useful in the compositions of this invention are well known and include the B-vitamins, Vitamin C, and minor vitamins such as bioflavonoids and biotin. The water-soluble trace elements include chromium, selenium, copper, calcium, zinc, magnesium and iron.

In addition, the compositions of the invention may also comprise conventional additives such as preservatives or antioxidants. Typical preservatives include methyl, ethyl, propyl or butyl paraben, benzalkonium chloride, chlorobutanol, thimerosal and the like, and are included at a concentration of about 0.01 to 0.3 weight percent. The antioxidants include α-tocopherol or salts thereof, EDTA and the like, and are used at concentrations between about 0.01 and 0.5 weight percent.

Because of the high particle surface area offered by the particulate products of this invention, the ingredients may be prone to oxidation, particularly if the content of unsaturated fatty acid moieties is high. In such cases, the compositions will preferably also contain α-tocopherol, α-tocopherol succinate or some other well known lipophilic antioxidant.

These emulsions are lyophilized to provide a fine essentially dry material, which can be stored without deterioration for a prolonged period of time, and which can be reconstituted to give a stable oil-in-water emulsion. Moreover, the lyophilized emulsion can be stored for a long term at ambient room temperature and which may be reconstituted to a fine submicron emulsion, which is exceedingly stable. After reconstitution, these emulsions may be used for oral, parenteral or topical applications, including ocular, transdermal, mucosal and for vaccinations or blood substitution, as well as for other pharmaceutical and cosmetic uses.

The submicron emulsion is generally composed of metabolized, synthetic or vegetable oil, preferably MCT oil (Medium Chain Triglycerides) emulsified with phospholipids and a synthetic co-emulsifier such as a non-ionic surfactant that has a polyoxyethylated moiety, preferably polyoxethylated oils, poloxamers or poloxamines. The submicron emulsion is adjusted for pH and isotonicity as needed. The submicron emulsion is protected by the amine group compound which, as noted, above, is preferably an amino acid or mixtures of amino acids. These emulsions can also include biocompatible polymers such as PVP, PVA or PEG as protective colloids and suspension or bulking agents.

Typical submicron emulsion formulations may be prepared with various oily phase concentrations, preferably from about 0.1 to 25 weight percent, but dilution has to be done to reduce oil concentration to below about 5%, preferably to below about 2%, before lyophilization, depending on mean droplet size required after reconstitution and provided that a protective agent, e.g., an amino compound in a concentration preferably above about 2% is added. Polyoxyethylated fatty acids (PLURONICs) can be used as co-emulsifiers and are apparently useful in combination with the amino compounds. The submicron emulsion may also contain antioxidants and preservatives.

An advantageous composition after combining the components and dilution with the water but before lyophilization is given below:

|  | w/v |
| --- | --- |
| MCT Oil | 1% |
| Glycine | 2% |
| Egg yolk phosphatides | 0.3% |
| Surfactant (EMULPHOR EL980) | 0.6% |
| Cryoprotectant (PVP 4000) | 0.2% |
| α-tocopherol | 0.006% |
| Preservatives | 0.1% |
| bioactive compound | 0.1% |
| Water for injection | to 100% |

The process for obtaining the dry emulsion contains two steps: preparation of the emulsion and freeze drying.

To prepare the emulsion, the oil soluble materials are dissolved in the oil phase and the water soluble materials are dissolved in the water phase. Optionally, some of the components, such as the cryoprotectants, preservatives or other additives can be dissolved after the emulsion is prepared.

The emulsion is prepared by high energy shear mixing of both phases at 40° to 85° C. (e.g., using a Polytron mixer at 15,000 rpm for 5 min., followed by APV Gaulin Lab 60 at 750 bar, for 5 min). The emulsion is diluted to an oil content of below about 5%, and preferably below about 2%, prior to freeze drying. This requires a typical addition of about 5 to 15 times (or more) as much water as in the emulsion, preferably between about 8 to 12 times. Optionally, the cryoprotectant, preservative or other components can be added to the diluted emulsion and then mixed with a magnetic stirrer. The final liquid preparation is adjusted to pH and osmolarity to the levels which are desired to be obtained after lyophilization and eventual reconstitution in the volume necessary to provide the required drug concentration.

The freeze-drying step is conducted on submicron emulsions which have a low oil concentration. Reconstitution is preferably with a smaller volume than the original one, in order to obtain the required oil and drug concentrations. Emulsion freezing can be obtained either by direct freezing at −10° C. or less, on the shelf of the lyophilizer or in a cool liquid at less than −10° C. (usually liquid nitrogen or ethanol with dry ice). Various freeze drying procedures according to the current art of lyophilization may be employed. The freeze-drying can be performed on bulk material or on aliquots of material in individual dosage form. Freezing rates do not appear to be critical to the lyophilization step. Closure may be performed under a nitrogen atmosphere inside the lyophilizer, or under vacuum, if desired.

The lyophilized submicron emulsion is designed to deliver bioactive compounds such as a drug, a prodrug, a peptide or a vaccine. The bioactive compound may be lipophilic, amphiphilic, sparingly water-soluble or water-insoluble, dissolved mostly in the oily phase or incorporated in the interface or the aqueous component with or without specific orientation.

Reconstitution is performed with sterile water for injection, if needed, or with a suitable solution and minor shaking is sufficient to produce a fine, stable, submicron emulsion. If desired, these submicron emulsions may be reconstituted with a smaller volume than the original one, in order to obtain the required oil and drug concentrations, as well as the desired osmolarity of the emulsion. The pH can also be adjusted as necessary or desired. As noted above, the reconstitution volume will generally be on the order of about 10 to 50% of the original volume, preferably about 15 to 40% and more preferably 25 to 35%. For example, after freeze-drying, reconstitution of the formulation shown above to one third of the initial volume will produce a 3% oil submicron emulsion.

The compositions of this invention are formulated for parenteral administration. By parenteral administration is meant routes of administration other than enteral and topical, usually by injection, and includes, without limitation, intravenous, intraarterial, intrathecal, perineural, intracardiac, intraperitoneal, transtracheal, intramuscular, subcutaneous, subcuticular, intraarticular, subcapsular, subarachnoid, and epidural injection. In designing parenteral delivery systems for the lyophilized compositions of this invention, provision must be made for separating the dry composition as provided herein from the intended aqueous pharmaceutical diluent. Accordingly, it may be preferred to simply package the lyophilized compositions separately, and reconstitute them at the time of use with commercially available Water for Injection, U.S.P.; 0.9% Sodium Chloride Injection, U.S.P.; 5% Dextrose Injection, U.S.P.; or a similar readily available pharmaceutical diluent.

Delivery systems for parenteral administration are usually divided into two categories: large volume parenteral ("LVP") delivery systems and small volume parenteral ("SVP") delivery systems. LVP delivery systems are commonly used when a large volume of fluid is required or desired to be given directly by the intravenous route, while small volume parenterals are commonly used to provide single or multiple injections via any of the above-mentioned routes. Also, a drug provided in an SVP delivery system can be added to an LVP delivery system to provide diluted, but continuous, intravenous administration of the drug.

LVP delivery systems commonly provide volumes of from 100 ml (which is considered an LVP dose for pediatric use) to 3000 ml. These volumes of fluid are available both in glass bottles and rigid, semi-rigid, and flexible containers fabricated from a variety of polymers and polymer combinations well known to the art. Each of these forms is suitable for use in the practice of the present invention, provided the usual safety and other standards for parenteral solution containers are met.

SVP delivery systems are also available in a variety of forms, depending upon the specific drug involved, its intended use, and the volume of fluid to be administered. SVP delivery systems typically contain from 0.1 ml to 100 ml of fluid. These delivery systems include glass and polymeric ampuls; glass and polymeric "fliptop" vials, which are intended for use in filling syringes; pressurized and unpressurized "pintop" vials, which incorporate a transfer cannula and are intended for use in adding the contents to LVP delivery systems; and a number of styles of prefilled syringes. Each is suitable for use in the practice of this invention, subject only to the usual criteria which dictate selection of such delivery systems, and the above-mentioned considerations regarding separation of the active dry component from the diluent until reconstitution.

EXAMPLES

Example 1

A submicron emulsion was prepared by mixing 4.25% MCT oil, 0.75% lecithin, 0.02% α-tocopherol, 2% PLURONIC F-68, 1.5% deoxycholic acid $Na^+$ salt and water up to 100%. The crude emulsion was then homogenized at 85° C. for 5 minutes by a Polytron homogenizer, followed by a Gaulin homogenizer for 5 min. at 750 Atm., to obtain a submicron emulsion. The emulsion was diluted with water to yield an oil concentration of 0.5% prior to lyophilization and glycine was added to achieve a glycine concentration of 6%.

The diluted submicron emulsion was frozen to below −60° C. within 2 min. and was transferred into a vacuum chamber of a lyophilizer. After 24 hours of lyophilization the dry substance was removed from the lyophilizer, sealed and stored at a room temperature until reconstitution.

The lyophilized emulsion, in dry form, was reconstituted with double distilled water to obtain an iso-osmolar emulsion. The mean droplet-size after reconstitution, was determined by a Coulter's nanosizer (N4SD model) which gives 0.28±0.09 μm, which are within the submicron size range discussed above. The maximum droplet size, as determined by light microscopy, was 1.5 μm. The droplet size of samples was measured at 5 minutes and 24 hours after reconstitution, and were essentially the same at each time.

Examples 2–6

Formulations were produced similar to Example 1, except that PVP was added before the lyophilization step. In Examples 2, 3, 4, 5 and 6 on the concentration of the PVP were 0.05%, 0.2%, 0.5%, 1.0% and 2.0% respectively. The results, which are given in Table 1, show that greater amounts of PVP help reduce the maximum droplet diameter without changing the mean droplet size.

TABLE 1

| Example No. | Compound - Concentrations | | | Results Mean droplet diameter & SD (in nm) | Max. droplet diam. (in μm) |
|---|---|---|---|---|---|
| | Gly % | PVP % | Oil % | | |
| 2 | 6 | 0.05 | 0.5 | 200 ± 60 | 1.5 |
| 3 | 6 | 0.2 | 0.5 | 200 ± 60 | 1.5 |
| 4 | 6 | 0.5 | 0.5 | 200 ± 60 | 1 |
| 5 | 6 | 1 | 0.5 | 200 ± 60 | 1 |
| 6 | 6 | 2 | 0.5 | 200 ± 60 | 1 |

Examples 7–10

Formulations were produced similar to Example 1, except that in these examples, the concentrations of the glycine were 1.5%, 3%, 4% and 5%, respectively, and that PVP was added to get a final concentration of 0.2% before the lyophilization step. The results, shown in Table 2, illustrate that increases in glycine reduce the maximum particle diameter of the emulsion droplets.

TABLE 2

| Example No. | Compound - Concentrations | | | Results Max. droplet diam. (in μm) |
|---|---|---|---|---|
| | Gly % | PVP % | Oil % | |
| 7 | 1.5 | 0.2 | 0.5 | 3 |
| 8 | 3 | 0.2 | 0.5 | 2.5 |
| 9 | 4 | 0.2 | 0.5 | 2 |
| 10 | 5 | 0.2 | 0.5 | 1.5 |

Examples 11–15

Formulations were produced similar to Example 1, except that, in Example 11, a final concentration of 0.2% PVP was added before the lyophilization step, and that in Examples 12, 13, 14 and 15 the oil concentration was 1%, 2%, 3% and 4%, respectively. The results, which are shown in Table 3, illustrate that the maximum droplet size increases with increasing oil content.

TABLE 3

| Example No. | Compound - Concentrations | | | Results Max. droplet diam. (in μm) |
|---|---|---|---|---|
| | Gly % | PVP % | Oil % | |
| 11 | 6 | 0.2 | 0.5 | 1 |
| 12 | 6 | 0.2 | 1 | 1 |
| 13 | 6 | 0.2 | 2 | 2 |
| 14 | 6 | 0.2 | 3 | 4 |
| 15 | 6 | 0.2 | 4 | 6 |

Examples 16–22

Formulations were produced similar to Example 1, except for the following changes:

The oil concentration For Examples 16–21 was 1%, while for Example 22, it was 2%.

A co-emulsifier, EMULPHOR EL-980, which is a nonionic surfactant, was added in a final concentration of 2% before the lyophilization step of each Example, but the PLURONIC F-68 and deoxycholic acid Na$^+$ salt were omitted.

In Examples 17 and 20, the concentration of glycine was 3%, while for Examples 18, 21 and 22, it was 6%.

PVP in a final concentration of 1% was added before the lyophilization step in Examples 19–22. The results, which are summarized in Table 4, show that glycine and PVP reduce the mean droplet size of the emulsion.

TABLE 4

| | Compound - Concentrations | | | | Results | |
|---|---|---|---|---|---|---|
| Example No. | EL 980 % | Gly % | PVP % | Oil % | Mean droplet diameter & SD (in nm) | Max. droplet diam. (in μm) |
| 16 | 2 | — | — | 1 | 582 ± 260 | 5 |
| 17 | 2 | 3 | — | 1 | 280 ± 100 | 2 |
| 18 | 2 | 6 | — | 1 | 268 ± 120 | 1 |
| 19 | 2 | — | 1 | 1 | 385 ± 140 | 3 |
| 20 | 2 | 3 | 1 | 1 | 300 ± 200 | 2 |
| 21 | 2 | 6 | 1 | 1 | 250 ± 100 | 1 |
| 22 | 2 | 6 | 1 | 2 | 280 ± 120 | 2 |

Examples 23–29

Formulations were produced similar to Examples 16–22 except that the oil concentration was 3% for Examples 23–28 and 4% for Example 29. The results are summarized in Table 5, and again show that glycine and PVP reduce the mean droplet size of the emulsion.

TABLE 5

| | Compound - Concentrations | | | | Results | |
|---|---|---|---|---|---|---|
| Example No. | EL 980 % | Gly % | PVP % | Oil % | Mean droplet diameter & SD (in nm) | Max. droplet diam. (in μm) |
| 23 | 2 | — | — | 3 | ND | 5 |
| 24 | 2 | 3 | — | 3 | 280 ± 100 | 4 |
| 25 | 2 | 6 | — | 3 | 300 ± 160 | 1.5 |
| 26 | 2 | — | 1 | 3 | ND | 10 |
| 27 | 2 | 3 | 1 | 3 | 540 ± 200 | 3 |
| 28 | 2 | 6 | 1 | 3 | 441 ± 140 | 1 |
| 29 | 2 | 6 | 1 | 4 | 470 ± 160 | 4 |

Examples 30–32

These formulations are similar to Example 11, except that a pilocarpine-base was added before the emulsification step to obtain a final concentration of 2%. After dilution, the concentration of pilocarpine in the formulations of Examples 30, 31 and 32 were 0.2%, 0.4% and 0.8%, respectively, and the oil concentrations were 0.5%, 1% and 2%, respectively. The results are seen in Table 6, and illustrate that decreasing the oil content decreases the size of the droplets of the emulsion.

TABLE 6

| | Compound - Concentrations | | | | Results | |
|---|---|---|---|---|---|---|
| Example No. | Gly % | PVP % | Submicron Pilocarpine emulsion | | Mean droplet diameter & SD (in nm) | Max. droplet diam. (in μm) |
| | | | % pilo | % oil | | |
| 30 | 6 | 0.2 | 0.2 | 0.5 | 285 ± 30 | 1 |
| 31 | 6 | 0.2 | 0.4 | 1 | ND | 2 |
| 32 | 6 | 0.2 | 0.8 | 2 | ND | 5 |

Examples 33–35

These formulations are similar to Examples 30–32, except that instead of adding a pilocarpine-base, indomethacin was added. The concentration of the indomethacin in Examples 33, 34 and 35 were 0.1%, 0.2% and 0.4%, respectively. The results are seen in Table 7, and again show the effect of glycine and PVP on the mean droplet size. In a similar manner, instead of pilocarpine or indomethacin additional experiments carried out with pharmaceutically active compounds such as diazepam, lidocaine, nifedipine and miconazol produce similar results.

TABLE 7

| | Compound - Concentrations | | | | Results | |
|---|---|---|---|---|---|---|
| Example No. | Gly % | PVP % | Submicron Pilocarpine emulsion | | Mean droplet diameter & SD (in nm) | Max. droplet diam. (in μm) |
| | | | % Indo | % oil | | |
| 33 | 6 | 0.2 | 0.1 | 0.5 | 220 ± 90 | 1 |
| 34 | 6 | 0.2 | 0.2 | 1 | ND | 3 |
| 35 | 6 | 0.2 | 0.4 | 2 | ND | 3 |

Examples 36–56

A submicron emulsion was prepared by mixing 4.25% MCT oil, 0.75% Lipoid E-80, 0.02% α-tocopherol succinate, 2% TWEEN-80 and water up to 100%. The crude emulsion was then homogenized at 40° C. for 5 minutes by a Polytron homogenizer, followed by a Gaulin homogenizer for 5 min. at 750 Atm.

The emulsion was diluted to yield 1% oil prior to lyophilization and ovalbumin hydrolysate was added to achieve an ovalbumin hydrolysate ("OAH") concentration of 2%. The total volume was 2 ml., and a 5 ml. serum bottle was used.

The diluted submicron emulsion was frozen below −35° C. in a freezer over several hours and was transferred into a vacuum chamber of a lyophilizer. After 24 hours of lyophilization the dry substance was removed from the lyophilizer, sealed and stored at room temperature until reconstitution.

The lyophilized emulsion, in dry form, was reconstituted with double distilled water to obtain iso-osmolar emulsion.

The mean droplet size after reconstitution was determined by a Coulter nanosizer (N4MD model) as 0.16±0.05 μm. The maximum droplet size was determined by light microscope.

Example 37 was similar to Example 36, except that the emulsion was diluted to an oil concentration of 2%, while in Example 38, the oil concentration was 0.5%, and in Example 39, it was 1%. In Examples 38 and 39, 1% OAH was added. Example 40 was similar to Example 36, except that the concentration of the oil was 2% and OAH was 1%.

Example 41 was similar to Example 38, except that polyvinylpyrrolidone (PVP) was added before the lyophilization step at a concentration of 1%. Example 42 was similar to Example 41, except that the concentration of the oil was changed to 1%.

Examples 41–46 are similar to Examples 37, 38, 41 and 42, respectively, but were frozen below –60° C. before lyophilization. Example 47 was similar to Example 46, except that the concentration of the oil was 2%.

Example 48 was similar to Example 39, except that the emulsion contained a different surfactant, 2% Tyloxapol, instead of 2% TWEEN-80. Example 49 was a similar preparation to that of Example 36, except that the emulsion contains 2% PLURONIC F-68 and 1% sodium deoxycholate instead of 2% TWEEN-80. Alanine glycine dipeptide (ALA-GLY) was added prior to the lyophilization, at a concentration of 6%, instead of OAH. The oil concentration was 0.5% after dilution. Example 50 was similar to Example 49, except that the glycine-D-asparagine (GLY-D-ASN) 6% was added instead of ALA-GLY.

Example 51 was similar to Example 36, except that ALA-GLY 6% was added prior to lyophilization instead of OAH and the oil concentration was 0.5% after dilution. Example 52 was similar to Example 51, except that glycine-glutamine dipeptide (GLY-GLN) 6% was added prior to lyophilization.

Example 53 was similar to Example 36, except that emulsion contains 0.4% adaprolol, an experimental soft beta adrenergic blocker, 1% Tyloxapol instead of 2% TWEEN-80 and, prior to lyophilization, GLY-D-ASN 6% was added instead of OAH. The oil concentration was 0.5%. Example 54 was similar to Example 53, except that the emulsion contained 2% TWEEN-80.

Results for Examples 36–48 are given in Table 8, while results for Examples 49–54 are given in Table 9.

TABLE 8

| Example No. | Compound - Concentrations | | | Results | |
|---|---|---|---|---|---|
| | OAH % | PVP % | OIL % | Max. droplet diameter (μm) | Mean droplet diameter ± SD N4MD (nm) |
| 36 | 2 | — | 1 | <2 | 158 ± 55 |
| 37 | 2 | — | 2 | <2 | 150 ± 45 |
| 38 | 1 | — | 0.5 | <2 | 142 ± 53 |
| 39 | 1 | — | 1 | <2 | 154 ± 46 |
| 40 | 1 | — | 2 | <2 | 152 ± 43 |
| 41 | 1 | 0.1 | 0.5 | <2 | 153 ± 43 |
| 42 | 1 | 0.1 | 1 | <2 | 157 ± 10 |
| 43 | 2 | — | 2 | <1 | 132 ± 45 |
| 44 | 1 | — | 2 | <1 | 119 ± 40 |
| 45 | 1 | 0.1 | 0.5 | <1 | 133 ± 50 |
| 46 | 1 | 0.1 | 1 | <1 | 123 ± 44 |
| 47 | 1 | 0.1 | 2 | <1 | 130 ± 10 |
| 48 | 1 | — | 1 | <2 | 130 ± 33 |

TABLE 9

| Example No. | Compound - Concentrations | | | | Results | |
|---|---|---|---|---|---|---|
| | ALA—GLY % | GLY—GLN % | GLY—D-ASN % | OIL % | Max. droplet diameter (μm) | Mean droplet diameter ± SD N4MD (nm) |
| 49 | 6 | — | — | 0.5 | <1 | 185 ± 54 |
| 50 | — | — | 6 | 0.5 | <2 | 175 ± 45 |
| 51 | 6 | — | — | 0.5 | <1 | 173 ± 56 |
| 52 | — | 6 | — | 0.5 | <2 | 188 ± 67 |
| 53 | — | — | 6 | 0.5 | <2 | 126 ± 45 |
| 54 | — | — | 6 | 0.5 | <2 | 190 ± 61 |

Example 55 was a submicron emulsion prepared by mixing 1.7% MCT oil, 0.3% Lipoid E-80, 0.02% α-tocopherol, 1.5% Emulphor EL-620 and purified water to make 100%. The materials were homogenized as per Example 1. To this emulsion, calcitonin, 10,000 U/ml, glycine 4% and PVP 1% were added. The mixture was frozen and lyophilized without prior dilution. The droplet size after reconstitution was 130±70 nm, as measured by a Coulter nanosizer (Model N4MD). Example 56 was similar to Example 55, but before the freezing step, 0.05% of Carbopol 940 was added. The droplet size after reconstitution was 125±52 nm.

While it is apparent that the invention herein disclosed is well calculated to fulfill the objects above stated, it will be appreciated that numerous modifications and embodiments may be devised by those skilled in the art, and is intended that the appended claims cover all such modifications and embodiments as fall within the true spirit and scope of the present invention.

What is claimed is:

1. A lyophilized composition comprising:

from about 0.2 to about 40 weight percent of an oil;

from about 40 to about 90 weight percent of a cryoprotectant, wherein said cryoprotectant comprises an amino compound and is present in an amount that is equal to or greater than the amount of said oil; and from about 0.1 to about 20 weight percent of an emulsifier;

the components being present in combination such that, when combined with an appropriate quantity of an aqueous liquid, the composition forms an oil-in-water emulsion; wherein the amino compound is selected from the group consisting of a straight amino acid, a branched amino acid, a nontoxic salt of a straight amino acid, a nontoxic salt of a branched amino acid, an ester of a straight amino acid, an ester of a branched amino acid, a peptide, and a protein hydrolysate.

2. The composition of claim 1 wherein the amino compound is glycine, leucine, isoleucine, lysine, methionine, phenylalanine, threonine, tryptophan, valine, alanine, arginine, histidine, proline, serine, tyrosine, taurine, carnitine, niacinamide or creatinine.

3. The composition of claim 1 wherein the oil is a vegetable oil, a synthetic oil, a mineral oil or a medium chain triglyceride oil or a mixture thereof and the emulsifier is lecithin.

4. The composition of claim 1 wherein the emulsifier is a phospholipid compound or a mixture of phospholipids.

5. The composition of claim 4 wherein the phospholipid is phosphatidylcholine, phosphatidylethanolamine or mixtures thereof.

6. The composition of claim 1 further comprising a co-emulsifier in an amount of from about 0.1 to about 20 weight percent.

7. The composition of claim 6 wherein the co-emulsifier is a non-ionic surfactant.

8. The composition of claim 7 wherein the non-ionic surfactant is a non-ionic alkylene oxide condensate of an organic compound which contains one or more hydroxyl groups.

9. The composition of claim 6, wherein the co-emulsifier is polyoxyethylated polymer conjugated with polyoxypropylene or a fatty acid.

10. The composition of claim 1 wherein the emulsifier is mono or diglyceride derivative.

11. The composition of claim 1 further comprising a suspension agent in an amount of from about 0.1 to 3 weight percent.

12. The composition of claim 11 wherein the suspension agent is polyvinyl alcohol, polyvinyl pyrrolidone, gelatin, pectin, methyl cellulose, glycols such as polyethylene or polypropylene glycols or mixtures thereof.

13. The composition of claim 1 further comprising a drug in the amount of about 0.01 to 2 weight percent.

14. The composition of claim 13 wherein the drug is selected from the group consisting of an antidepressant, an anticonvulsant, a narcotic analgesic, a narcotic antagonist, a nonsteroidal antiinflammatory drug, a sympathomimetic agent, a parasympathomimetic agent, an antimuscarinic agent, an adrenergic blocking agent, digitalis, a diuretic, an antimicrobial agent, an antineoplastic agent, a vaccine, an oxygen carrier, a hormone, a hormone antagonist, a fat-soluble vitamin and a combination thereof.

15. A lyophilized composition comprising:

from about 0.2 to about 30 weight percent of an oil;

from about 50 to about 75 weight percent of a cryoprotectant, wherein said cryoprotectant comprises an amino compound selected from the group consisting of a straight amino acid, a branched amino acid, a nontoxic salt of a straight amino acid, a nontoxic salt of a branched amino acid, an ester of a straight amino acid, an ester of a branched amino acid, a peptide, and a protein hydrolysate and being present in an amount that is equal to or greater than the amount of said oil;

from about 0.1 to about 10 weight percent of an emulsifier; and from about 0.1 to about 10 weight percent of a co-emulsifier;

the components being present in combination such that, when combined with an appropriate quantity of an aqueous liquid, the composition forms an oil-in-water emulsion.

16. An oil-in-water emulsion comprising water, about 0.2 to 25 weight percent of an oil, about 0.1 to 5 weight percent of an emulsifier, and about 0.25 to 50 weight percent of a cryoprotectant, wherein said cryoprotectant comprises an amino compound selected from the group consisting of a straight amino acid, a branched amino acid, a nontoxic salt of a straight amino acid, a nontoxic salt of a branched amino acid, an ester of a straight amino acid, and ester of a branched amino acid, a peptide, and a protein hydrolysate and being present in an amount that is equal to or greater than the amount of said oil.

17. The emulsion of claim 16 wherein the oil is a medium chain triglyceride oil, a vegetable oil, a mineral oil or mixtures thereof, the emulsifier is lecithin and the weight ratio of the amino compound to the first component is between 1/1 and 20/1.

18. The emulsion of claim 16 wherein the emulsifier is a phospholipid compound or a mixture of phospholipids.

19. The emulsion of claim 18 wherein the phospholipid is phosphatidylcholine, phosphatidylethanolamine or mixtures thereof.

20. The emulsion of claim 16 further comprising a co-emulsifier in an amount of about 0.1 to 5%.

21. The emulsion of claim 20 wherein the co-emulsifier is a non-ionic surfactant.

22. The emulsion of claim 16 further comprising a suspending agent in an amount of between about 0.1 and 5%.

23. The emulsion of claim 16 further comprising an effective amount of a preservative or antioxidant.

24. The emulsion of claim 16 further comprising a drug in the amount of about 0.01 to 2%.

25. The emulsion of claim 24 further comprising an effective amount of an additional drug.

26. The emulsion of claim 16 in the form of a submicron emulsion having a mean droplet size of about 0.05 to 0.5 μm.

27. The emulsion of claim 16 wherein the amino compound is present in an amount of between about 0.5 to 12%, the oil is present in an amount of about 0.4% to 10%, the emulsifier is present in an amount of about 0.2 to 4%, the weight ratio of the amino compound to the oil is between about 1/1 and 15/1 and the emulsion is a submicron emulsion having a mean droplet size of between about 0.1 and 0.3 μm.

28. The emulsion of claim 20 wherein the amino compound is present in an amount of between about 1 to 10%, the oil is present in an amount of about 0.6% to 8%, the emulsifier is present in an amount of about 0.25 to 2.5%, the co-emulsifier is present in an amount of about 0.25 to 2.5%, the weight ratio of the amino compound to the oil is between about 1/1 and 12.5/1 and the emulsion is a submicron emulsion having a mean droplet size of between about 0.1 and 0.3 μm.

29. A lyophilized composition made by formulating the emulsion of claim 16, diluting the emulsion to reduce the percentage by weight of the oil content thereof, and lyophilizing the reduced oil content emulsion to form a lyophilized composition.

30. A lyophilized composition made by formulating the emulsion of claim 27, diluting the emulsion to reduce the percentage by weight of the oil content thereof, and lyophilizing the reduced oil content emulsion to form a lyophilized composition.

31. A lyophilized composition made by formulating the emulsion of claim 28, diluting the emulsion to reduce the percentage by weight of the oil content thereof, and lyophilizing the reduced oil content emulsion to form a lyophilized composition.

32. The emulsion of claim 27, wherein the weight ratio of the amino compound to the oil is between 1/1 and 15/1.

33. The emulsion of claim 28, wherein the weight ratio of the amino compound to the oil is between 1/1 and 12.5/1.

34. The composition of claim 13 wherein the drug is selected from the group consisting of an anticholinesterase agent, a ganglionic stimulating agent, a ganglionic blocking agent, a neuromodulator, an antibody, an immunomodulator, hemoglobin and a combination thereof.

35. The composition of claim 13 wherein the drug is selected from the group consisting of an anesthetic, a saluretic, an antiviral agent, an antifungal agent, an immunosuppressant and a combination thereof.

36. The composition of claim 13 wherein the drug is selected from the group consisting of an anxiolytic, a neuromuscular blocking agent and a combination thereof.

37. The composition of claim 13 wherein the drug is selected from the group consisting of a sedative, an autacoid agent, an autacoid antagonist and a combination thereof.

38. A lyophilized composition consisting essentially of:

from about 0.2 to about 40 weight percent of an oil;

from about 40 to about 90 weight percent of a cryoprotectant, wherein said cryoprotectant comprises an amino compound selected from the group consisting of a straight amino acid, a branched amino acid, a nontoxic salt of a straight amino acid, a nontoxic salt of a branched amino acid, an ester of a straight amino acid, an ester of a branched amino acid, a peptide, and a protein hydrolysate and being present in an amount that is equal to or greater than the amount of said oil; and from about 0.1 to about 20 weight percent of an emulsifier, wherein the components being present in combination such that, when combined with an appropriate quantity of an aqueous liquid, the composition forms an oil-in-water emulsion.

39. A lyophilized composition comprising:

from about 0.2 to about 30 weight percent of an oil;

from about 50 to about 75 weight percent of a cryoprotectant, wherein said cryoprotectant comprises an amino compound selected from the group consisting of a straight amino acid, a branched amino acid, a nontoxic salt of a straight amino acid, a nontoxic salt of a branched amino acid, an ester of a straight amino acid, an ester of a branched amino acid, a peptide, and a protein hydrolysate and being present in an amount that is equal to or greater than the amount of said oil;

from about 0.1 to about 10 weight percent of an emulsifier; and from about 0.1 to about 10 weight percent of a co-emulsifier;

wherein the composition is formed by lyophilizing an emulsion of the components after dilution of the emulsion to reduce that oil content thereof, with the components of the lyophilized composition being present in combination such that, when combined with an appropriate quantity of an aqueous liquid, the composition forms an oil-in-water emulsion.

* * * * *